US011257259B2

(12) United States Patent
Teixeira et al.

(10) Patent No.: US 11,257,259 B2
(45) Date of Patent: Feb. 22, 2022

(54) TOPOGRAM PREDICTION FROM SURFACE DATA IN MEDICAL IMAGING

(71) Applicant: Siemens Healthcare GmbH, Erlangen (DE)

(72) Inventors: Brian Teixeira, Verneuil-en-Halatte (FR); Vivek Kumar Singh, Princeton, NJ (US); Birgi Tamersoy, Erlangen (DE); Terrence Chen, Princeton, NJ (US); Kai Ma, Princeton, NJ (US); Andreas Krauss, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 82 days.

(21) Appl. No.: 16/040,998

(22) Filed: Jul. 20, 2018

(65) Prior Publication Data

US 2019/0057521 A1   Feb. 21, 2019

Related U.S. Application Data

(60) Provisional application No. 62/545,554, filed on Aug. 15, 2017.

(51) Int. Cl.
*G06T 11/00* (2006.01)
*A61B 5/0515* (2021.01)
(Continued)

(52) U.S. Cl.
CPC .......... *G06T 11/003* (2013.01); *A61B 5/0033* (2013.01); *A61B 5/055* (2013.01);
(Continued)

(58) Field of Classification Search
CPC ........... G06N 3/04; G06T 2207/20081; A61M 2205/3592
USPC .................. 340/539.26, 286.02; 726/22, 23; 709/224, 220, 222; 600/424, 425, 439, 600/467
See application file for complete search history.

(56) References Cited

U.S. PATENT DOCUMENTS

| 2010/0217119 A1* | 8/2010 | Forster ................. A61B 5/0536 600/425 |
| 2013/0166256 A1* | 6/2013 | Wirx-Speetjens ...... G06F 17/50 703/1 |

(Continued)

FOREIGN PATENT DOCUMENTS

| WO | 2013072810 A1 | 5/2013 |
| WO | 2016073841 A1 | 5/2016 |

OTHER PUBLICATIONS

Badrinarayanan, Vijay, Alex Kendall, and Roberto Cipolla. "Segnet: A deep convolutional encoder-decoder architecture for image segmentation." arXiv preprint arXiv:1511.00561 (Oct. 2016), pp. 1-14.
(Continued)

*Primary Examiner* — Kiet M Doan

(57) ABSTRACT

For topogram predication from surface data, a sensor captures the outside surface of a patient. A generative adversarial network (GAN) generates the topogram representing an interior organ based on the outside surface of the patient. To further adapt to specific patients, internal landmarks are used in the topogram prediction. The topogram generated by one generator of the GAN may be altered based on landmarks generated by another generator.

20 Claims, 5 Drawing Sheets

(51) Int. Cl.
| | |
|---|---|
| G06T 5/00 | (2006.01) |
| A61B 5/00 | (2006.01) |
| G06N 3/04 | (2006.01) |
| G06N 3/08 | (2006.01) |
| A61B 5/055 | (2006.01) |
| G06K 9/62 | (2022.01) |
| A61B 90/00 | (2016.01) |
| G16H 30/20 | (2018.01) |
| G06N 20/00 | (2019.01) |
| A61B 6/00 | (2006.01) |
| G06T 7/00 | (2017.01) |
| A61B 5/107 | (2006.01) |

(52) U.S. Cl.
CPC ............ *A61B 5/0515* (2013.01); *A61B 6/463* (2013.01); *A61B 6/5205* (2013.01); *A61B 6/545* (2013.01); *A61B 90/361* (2016.02); *G06K 9/6262* (2013.01); *G06K 9/6274* (2013.01); *G06N 3/0445* (2013.01); *G06N 3/0454* (2013.01); *G06N 3/084* (2013.01); *G06N 20/00* (2019.01); *G06T 5/00* (2013.01); *G06T 7/0014* (2013.01); *G16H 30/20* (2018.01); *A61B 5/107* (2013.01); *G06K 2209/055* (2013.01); *G06T 2207/10028* (2013.01); *G06T 2207/10116* (2013.01); *G06T 2207/20081* (2013.01); *G06T 2207/20084* (2013.01)

(56) References Cited

U.S. PATENT DOCUMENTS

| | | | | |
|---|---|---|---|---|
| 2013/0188770 | A1* | 7/2013 | McNitt-Gray | A61B 6/545 378/16 |
| 2014/0314205 | A1* | 10/2014 | Carelsen | A61B 6/4458 378/62 |
| 2015/0089399 | A1* | 3/2015 | Megill | G06Q 30/0203 715/753 |
| 2016/0306924 | A1* | 10/2016 | Singh | G16H 30/20 |
| 2016/0310739 | A1* | 10/2016 | Burdick | A61B 5/407 |
| 2017/0095223 | A1* | 4/2017 | Tian | A61B 6/032 |
| 2017/0116776 | A1* | 4/2017 | Aughey | G06T 19/00 |
| 2017/0316281 | A1* | 11/2017 | Criminisi | G06K 9/627 |
| 2018/0122082 | A1* | 5/2018 | Mukherjee | G06N 3/0454 |
| 2018/0132725 | A1* | 5/2018 | Vogl | A61B 3/0025 |
| 2018/0144466 | A1* | 5/2018 | Hsieh | G06F 19/00 |
| 2018/0153437 | A1* | 6/2018 | Schwartz | A61B 5/068 |

OTHER PUBLICATIONS

Goodfellow, Ian, et al. "Generative adversarial nets." Advances in neural information processing systems. Jun. 2014, pp. 1-9.

Isola, Phillip, et al. "Image-to-image translation with conditional adversarial networks." arXiv preprint (Nov. 2017), pp. 1-17.

Long, Jonathan, Evan Shelhamer, and Trevor Darrell. "Fully convolutional networks for semantic segmentation." Proceedings of the IEEE conference on computer vision and pattern recognition. 2015, pp. 1-10.

Newell, Alejandro, Kaiyu Yang, and Jia Deng. "Stacked hourglass networks for human pose estimation." European Conference on Computer Vision. Springer, Cham, 2016, pp. 1-17.

Ronneberger, Olaf, Philipp Fischer, and Thomas Brox. "U-net: Convolutional networks for biomedical image segmentation." International Conference on Medical image computing and computer-assisted intervention. Springer, Cham, 2015, pp. 1-8.

Singh, Vivek, et al. "Darwin: Deformable patient avatar representation with deep image network." International Conference on Medical Image Computing and Computer-Assisted Intervention. Springer, Cham, 2017, pp. 1-8.

Zeiler, Matthew D. "ADADELTA: an adaptive learning rate method." arXiv preprint arXiv:1212.5701 (Dec. 2012), pp. 1-6.

Snehashis, Roy, et al., "Synthesizing CT from Ultrashort Echo-Time MR Images via Convolutional Neural Networks", 26.9.2017, medical image computing and computer-assisted intervention—MICCAI 2015 : 18th international conference, Munich, Germany, Oct. 5-9, 2015, proceedings, CH, SP047449020, ISSN: 0302-9743, ISBN: 978-3-319-24946-9.

Teixeira, Brian, et al., "Generating Synthetic X-ray Images of a Person from the Surface Geometry", arxiv.org, cornell University Library, 14853, Jan. 5, 2018, XP080884751.

Ronneberger, Olaf et al. "U-Net: Convolutional networks for biomedical image segmentation" 18th International Conference on Medical Image Computing and Computer-Assisted Intervention 2015 (MICCAI 2015); pp. 234-241, Oct. 5-9, 2015.

* cited by examiner

TOPOGRAM PREDICTION FROM SURFACE DATA IN MEDICAL IMAGING

RELATED APPLICATION

The present patent document claims the benefit of the filing date under 35 U.S.C. § 119(e) of Provisional U.S. Patent Application Ser. No. 62/545,554, filed Aug. 15, 2017, which is hereby incorporated by reference.

BACKGROUND

The present embodiments relate to estimating a topogram for medical imaging. There have been advances in realistic human body shape modeling and simulation in the graphics domain. Different statistical models have been applied to learn compact parametric representations of the human body shape. However, their impact on the healthcare domain is relatively limited. Existing shape modeling approaches focus primarily on the skin surface while the healthcare domain pays more attention to the internal organs.

SUMMARY

Systems, methods, and instructions on computer readable media are provided for topogram predication from surface data. A sensor captures the outside surface of a patient. A generative adversarial network (GAN) generates the topogram representing interior organs based on the outside surface of the patient. To further adapt to specific patients, internal landmarks are used in the topogram prediction. The topogram generated by the generator of the GAN may be altered based on landmarks generated by another generator.

In a first aspect, a method is provided for topogram prediction from surface data in a medical imaging system. The topogram represents an internal organ of the patient as a projection through the patient. A sensor captures an outer surface of a patient. An image processor generates the topogram by a machine-learned generative adversarial network in response to input of the surface data to the machine-learned generative adversarial network. The surface data is from an output of the sensor for the outer surface. A display device displays the topogram.

In a second aspect, a method is provided for topogram prediction from surface data in a medical imaging system. A sensor captures an outer surface of a patient. An image processor generates the topogram with first and second machine-learned networks in response to input of the surface data to the first and second machine-learned networks. The surface data is from an output of the sensor for the outer surface. The topogram represents an internal organ of the patient as a projection through the patient. The first machine-learned network outputs a spatial markers map, and the second machine-learned network outputs the topogram based on the surface data and the spatial markers map. A display device displays the topogram.

In a third aspect, a medical imaging system is provided for topogram prediction. A depth sensor is configured to measure depths to a patient. An image processor is configured to apply a machine-learned generator of a trained generative adversarial network to depth information from the depths. The machine-learned generator was trained to generate the topogram from the depth information. A display is configured to display the topogram.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Figure 1:
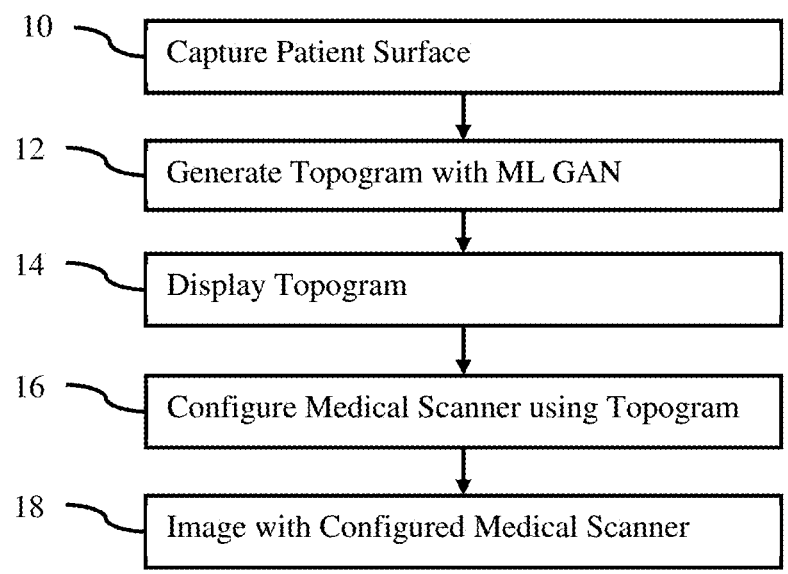
FIG. 1 is a flow chart diagram of one embodiment of a method for topogram prediction from surface data in a medical imaging system.

The internal anatomy of a human body is estimated from the surface data. A computational topogram is predicted from patient surface data. For example, a synthetic X-ray image of a person is generated only from the surface geometry or depth camera measurements. The topogram, a 2D projection of the internal anatomy of a patient, is predicted from geometric measurements on the patient's body surface using deep machine learning algorithms. To capture physical correctness of the topogram, Deep Generative Adversarial Networks are used. The proposed architecture may capture nonlinear correlation between the surface data and internal anatomy. The machine-learned networks may be Wasserstein GANs (WGAN) trained with a gradient penalty method for a conditional regression task. The synthetic X-ray serves as an approximation of the true internal anatomy.

Markers may be predicted, allowing adjustment to update the X-ray image. With the proposed framework, synthetic X-ray images may easily be generated by varying surface geometry. By perturbing the parameters, additional synthetic X-ray images may be generated from the same surface geometry. As a result, the training data barrier in the medical domain is overcome by producing many X-ray images through parameter adjustment. Since the markers serve as spatial parameters to perturb the image, the predicted image of the internal anatomy is a parametrized image. The predicted topogram may be manipulated using body markers distributed across the body. For example, if the predicted lung appears short, then a body marker near the lung region may be manipulated to adjust its position, and the topogram will be updated in a physically consistent manner.

In one embodiment, parametrized images are generated using a convergent training pipeline. As the training framework learns to predict images and the corresponding spatial parameters (i.e. markers), the framework also needs to ensure that the perturbations of these parameters lie on a manifold of 'realistic deformations' (e.g. realistic facial expressions when generating face images or realistic body anatomy when generating synthetic X-ray). Since learning such output spaces, which are implicitly highly correlated, is difficult, a pair of networks is trained, one trained to predict the parameters from image contents and the other trained to predict the image contents from the parameters. When the parameters are updated, the networks are applied iteratively in a loop until convergence. To facilitate such convergent behavior during test phase, both networks are jointly learnt. A bijection between the predicted markers and the generated images is explicitly learned.

The predicted topogram may be useful for teaching purposes, such as generating topogram images as samples to be used in machine training to avoid a data barrier of too few samples for training. The predicted topogram may be used for scan planning. For example, the generated topogram is used for more precise positioning compared to just using body markers. Furthermore, positioning suggested by the system using a physically consistent generated topogram may be more readily used by radiographers as opposed to just the body marker points. The topogram may be used for detection of anomalies, patient positioning, interventional procedures, completion of a full X-ray from a partial X-ray image, or other uses.

Computed tomography or X-ray based topogram prediction is provided in the examples below. Other modes of medical imaging may be used, such as predicting the topogram for magnetic resonance, positron emission tomography, single photon emission computed tomography, or ultrasound scans.

FIG. 1 is a flow chart diagram of one embodiment of a method for topogram prediction from surface data in a medical imaging system. A machine-learned GAN is used to generate a topogram from data representing an outside of the patient. The topogram represents internal organs of the patient as a projection through the patient, such as a CT or X-ray topogram.

The method is performed in the order shown (e.g., top to bottom or numerical), but other orders may be used. Additional, different or fewer acts may be provided. For example, acts 16 and/or 18 are not provided. In another example, act 14 is not provided as the topogram is one of many used for machine training or is used to configure for imaging without viewing by the operator.

In act 10, a sensor captures an outer surface of a patient. The sensor is a depth sensor, such as a 2.5D or RGBD sensor (e.g., Microsoft Kinect 2 or ASUS Xtion Pro). The depth sensor may be a camera or cameras capturing a grid projected onto the patient. Multiple cameras may reconstruct an outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient from head to toe and hand to hand on one side or just the torso.

The outer surface is the skin of the patient. In other embodiments, the outer surface includes clothing. The sensor may use a frequency that passes through clothing and detects skin surface.

The outer surface is captured as depths from the sensor to different locations on the patient, an image or photograph of the outside of the patient, or both. The sensor outputs the sensed image and/or depths. Alternatively, the sensor measurements are processed to determine the outer surface information, such as stereoscopically determining the outer surface from camera images from different angles with image processing.

The measurements of the outer surface from the sensor are surface data for the patient. In one embodiment, the measurements or other output of the sensor are used to determine the surface data. The output is processed to determine the surface data. For example, a statistical shape model is fit to the depths. The statistical shape model is a mesh or other representation of an average or other statistical representation of an outside of a human or part of a human. The statistical shape model includes probabilities or other constraints on alteration, so that the fitting maintains the shape based on statistics. The surface data is then determined from the fit statistical shape model, such as depths from a point to the model.

The surface data may include different representations of the patient, such as the depths from the fit model and a projection of the outer surface (e.g., a camera image) or a thickness. The thickness may be a difference of a given depth from the maximum and minimum depth for the model or the depths from the sensor. For example, given a 3D surface mesh of a patient, 2D projections of the data are generated as a skin surface image and a depth image. As another example, the 3D human surface mesh data is represented with a 2-channel 2D image—the first channel stores the depth of the body surface as observed from front, and second channel stores the thickness computed by measuring the distance between the closest and furthest point as observed from front. Other surface data may be used.

The topogram image is predicted from the surface data. The topogram shows the atlas of the internal patient anatomy. The topogram may be predicted from only the surface data or may be predicted from the surface data and other data, such as patient height, weight, or body mass index.

Figure 2:
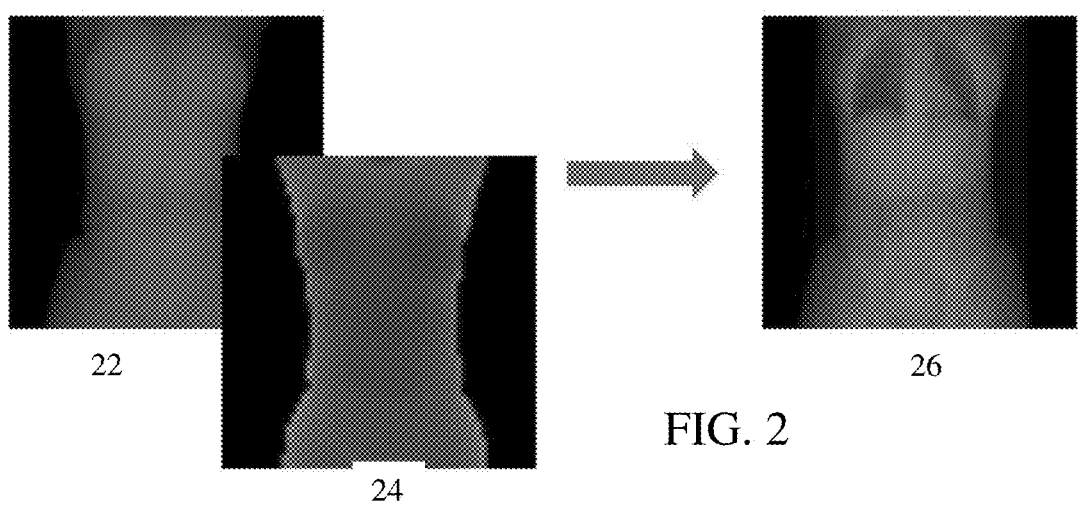
FIG. 2 illustrates example 2-channel surface data for predication of a topogram.

In act 12, an image processor generates the topogram. The surface data with or without other data are input to a machine-learned network and scalar or display values for the topogram are output. For example, a projection image and depth image of the outer surface are input as two channels to the machine-learned network, which outputs a synthetic X-ray image (i.e., an X-ray projection) in response to the input. FIG. 2 shows an example where a surface depth image 24 and a surface projection image 22 are input to output a topogram 26. The image processor applies the machine-learned network for topogram prediction. Any inputs for which the network is trained to use are applied as an input feature vector, such as just the surface data.

The machine-learned network is an image-to-image network, such as a generative adversarial network, trained to convert surface data to a topogram. For example, the trained convolution units, weights, links, and/or other characteristics of the network are applied to the surface data and/or derived feature values to extract the corresponding features through a plurality of layers and output the topogram. The features of the input images (e.g., surface data) are extracted from the images. Other more abstract features may be extracted from those extracted features using the architecture. Depending on the number and/or arrangement of units or layers, other features are extracted from the input.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

Figure 3:
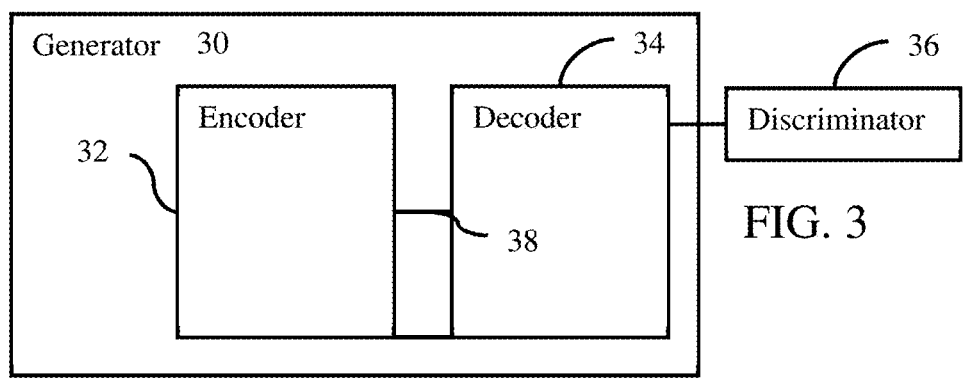
FIG. 3 is a block diagram of one embodiment of a GAN.

The machine learning network is an image-to-image network. Any machine training architecture for outputting a spatial distribution from an input spatial distribution may be used. For example, U-Net is used. A convolutional-to-transposed-convolutional network is used. One segment of layers or units applies convolution to increase abstractness or compression. The most abstract feature values are then output to another segment. The other segment of layers or units then applies transposed-convolution to decrease abstractness or compression, resulting in outputting of a topogram or indication of class membership by location. FIG. 3 shows an example fully convolutional network as a GAN. The GAN includes a generator 30, such as the image-to-image or U-Net, and a discriminator 36. The generator 30 includes an encoder (convolutional) network 32 and decoder (transposed-convolutional) network 34 forming a "U" shape with a connection between passing features at a greatest level of compression or abstractness from the encoder 32 to the decoder 34. Any now known or later developed U-Net architectures may be used. Other fully convolutional networks may be used.

For applications, the generators 30 of the GANs are used without the discriminator 36. The GANs are applied to the patient surface data by the generator 30 without the discriminator 36. The discriminator 36 is used for training.

The GAN is a deep architecture, which may include convolutional neural network (CNN) or deep belief nets (DBN). Other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Rather than pre-programming the features and trying to relate the features to attributes, the deep architecture is defined to learn the features at different levels of abstraction based on an input image with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape or building indication. For transposed-convolution to reconstruct, the level of abstraction reverses. Each unit or layer reduces the level of abstraction or compression.

The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Max pooling, upsampling, downsampling, and/or softmax layers or units may be used. Different units may be of the same or different type.

In one embodiment, the topogram prediction is treated as a classic image-to-image translation problem. Starting from 2 channel images (e.g., skin surface and depth to skin image), a single channel image of the same size (topogram image) is regressed. This approach provides a network able to capture the features in the input image to retrieve the output image, which consists, in a sense, of a more 'complete' version of the input. A Fully Convolutional Networks (FCN) may be used, such as the generator 30 with the encoder 32 and the decoder 34. The encoder 32 'encodes' the useful features of the input needed to regress the target, while the decoder 34 tries to use these features to create the targeted image.

In one embodiment, the generator 30 is a U-Net with one or more skip connections 38. The skip connections 38 pass features from the encoder 32 to the decoder 34 at other levels of abstraction or resolution than the most abstract (i.e. other than the bottleneck). Skip connections 38 provide more information to the decoding layers. A Fully Connected layer may be at the bottleneck of the network (i.e., between the encoder 32 and decoder 34 at a most abstract level of layers).

The fully connected layer may make sure as much information as possible is encoded. Batch normalization may be added to stabilize the training.

Figure 4:
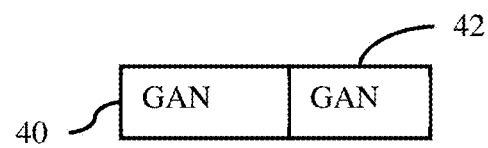
FIG. 4 shows an example stacking of two GANs.

In another embodiment, multiple U-Nets, generators 30 or GANs are stacked. For example, the generators 30 of GANs 40, 42 are stacked sequentially as shown in FIG. 4. The output from one GAN 40 provides an input to the other GAN 42, which outputs the topogram. The initial GAN 40 receives the surface data as an input. Stacking U-Nets as the generators 30 helps capture more details for the topogram. The patient's shape may be regressed with more details, such as details around or other lungs.

A more realistic topogram image may result from using a GAN than from a U-net or generator 30 trained without a discriminator 36. GANs generate realistic images in image-to-image translation problems. GANs train two different networks simultaneously, the discriminator 36 whose purpose is to decide whether a given image is real or fake, and the generator 30 whose purpose is to fool the discriminator 36 by making images as realistic as possible.

The basic approach for training a GAN is to update the discriminator 36 with both generated and real images, freeze weights in the discriminator 36, and then update the generator 30 on how good the generator 30 is at fooling the discriminator 36. Weights in the generator 30 are updated while minimizing the binary cross entropy loss of the discriminator 36 where output is supposed to be always 1. In one embodiment, the GAN is trained from an initial state based on estimates. In another embodiment, the whole regressor model or generator 30 is not trained from scratch, but a previously trained generator 30 is updated by learning the missing details. The missing details may be reconstructed by adding a residual to the generated images. Therefore, a residual image with the same resolution as the generated image is learned. An element-wise sum of the residual and the generated image and an adversarial loss to update the residual are computed. The pre-trained generator 30 is not updated, and the residual network would take as an input the bottleneck of the regressor model, e.g. the encoded features at the most abstract level. IN alternative embodiments, the pre-trained generator 30 is updated.

For training any of the networks, various optimizers may be used, such as Adadelta, SGD, RMSprop, or Adam. The weights of the network are randomly initialized, but another initialization may be used. End-to-end training is performed, but one or more features may be set. Batch normalization, dropout, and data augmentation are not used, but may be (e.g., using batch normalization and dropout). During the optimization, the different distinguishing features are learned. The features providing an indication of flow given input medical image of anatomy or tissue are learned.

The optimizer minimizes an error or loss, such as the Mean Squared Error (MSE), Huber loss, L1 loss, or L2 loss. The Huber loss may be less sensitive to outliers in data (represented in the training set by big variations in shape). Use of Huber loss helps capture better context. The patient's shape may be regressed better. In another embodiment, an L1 loss is used to better define lungs or other organs represented in the generated topogram. Using the stacked U-Nets with L1 loss, the patient's shape and details for the lungs or other organs may be better than for Huber or L2 loss.

Figure 5:
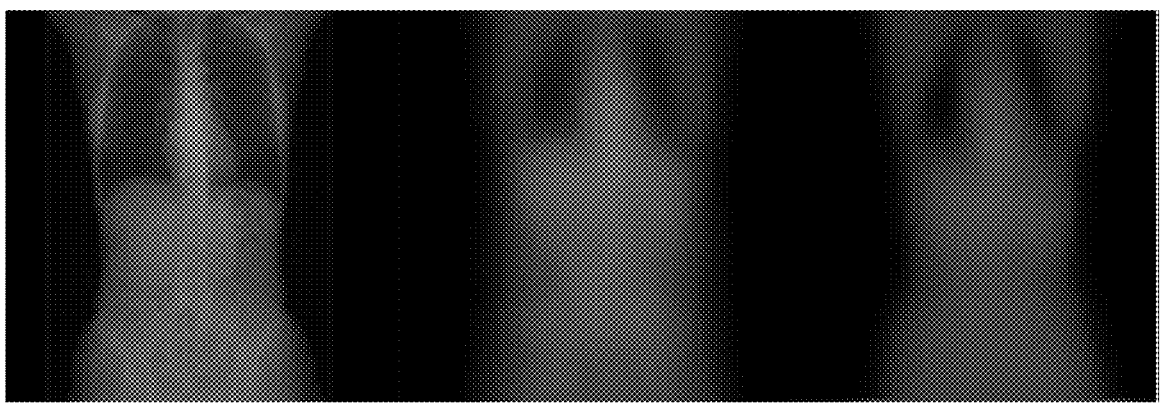
FIG. 5 shows a ground truth topogram and two generated topograms based on different loss functions using a fully convolutional network.
Figure 6:
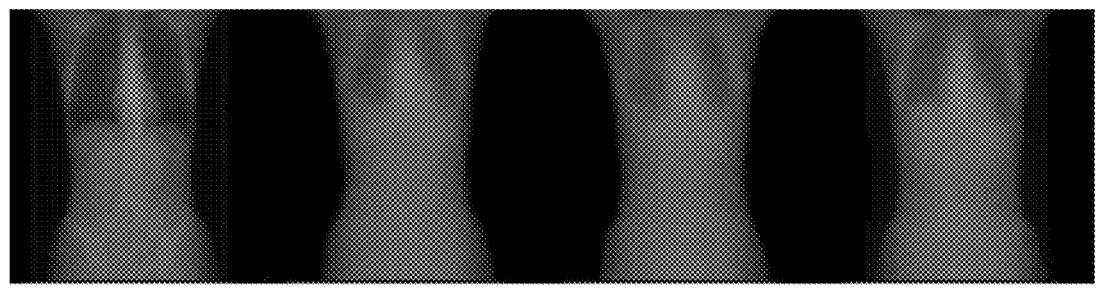
FIG. 6 shows a ground truth topogram and three generated topograms based on different loss functions for stacked U-nets.
Figure 7:
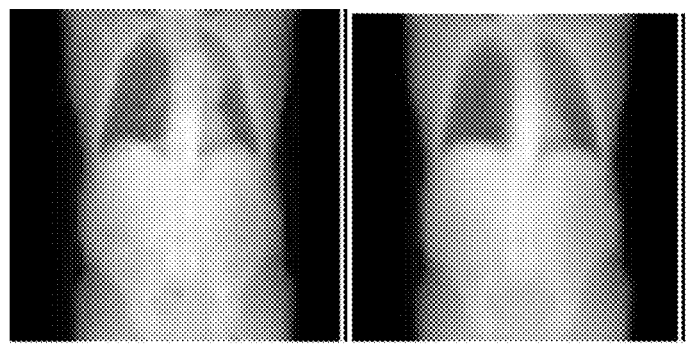
FIG. 7 shows a ground truth topogram and a generated topogram based on a GAN.

FIG. 5 shows a ground truth topogram generated with a CT scan on the left, a topogram from a fully convolutional network trained with L2 loss in the middle, and a topogram from a fully convolutional network trained with a Huber loss on the right. FIG. 6 shows a ground truth topogram on the left, and three images from a U-net with skip connections trained with L2 (center left), Huber (center right), and L1 (right) losses. The L1 loss results in greater detail for the lungs and provides for the shape of the patient. The mean square error of the L1 loss is $1.27 \cdot 10^{-3}$, for the L2 loss is $2.28 \cdot 10^{-3}$, and for the Huber loss is $2.21 \cdot 10^{-3}$. The high contrast images of FIG. 6 show that the U-Net with L1 loss captures more details, especially for the bones. FIG. 7 shows a ground truth image on the left and a GAN generated topogram on the right, showing more detail and the body shape.

Once trained, the model may be applied to estimate a topogram from input surface data. The many samples in the training data (e.g., surface data and ground truth topograms) are used to learn to output the topogram. The machine learning model is trained to learn the correspondence between the surface data and the topogram.

Other information may be used in topogram prediction. In one embodiment, stacked networks are used. Rather than focus on topogram regression in both GANs 40, 42, the stacked network uses at least one GAN to predict one or more internal body markers. External body markers may be detected or predicted. The input surface data as well as the predicted internal body markers are used to predict topogram by another GAN. The predicted body markers may be adjusted, which would automatically update the topogram.

Figure 8:
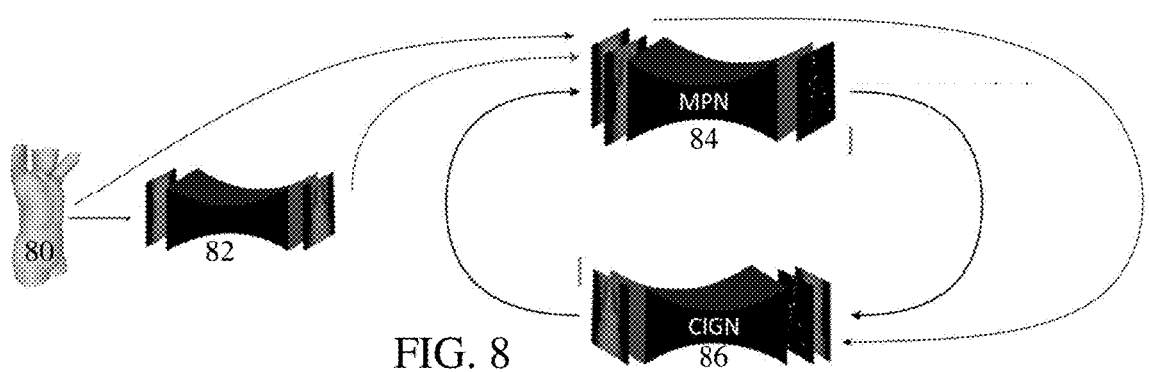
FIG. 8 shows an example embodiment of stacked networks with landmark prediction included as part of topogram prediction.

FIG. 8 shows an example. The network is a marker prediction network, and the GAN 86 is a conditional image generation network for predicting the topogram (e.g., X-ray projection image). This stacked network 84 is trained using GAN. Only the generators are stacked, and training may use only one discriminator. The stacked network takes as input a 2-channel image (e.g., depth image and skin surface of the surface data), which goes through the landmark regressor predicting an N channel image where N is the number of landmarks. These N channel images are concatenated with the 2-channel image of the surface data to form an N+2 channel image that goes through the topogram regressor predicting a single channel image as the topogram.

The network for landmark detection may be a pre-trained landmark regressor. As the GAN 86 for predicting the topogram is trained, the weights of the network for landmark detection are not updated. During training, the ground truth landmark images may be used for training the GAN 86 for the topogram rather than landmark images output by the network 84 for landmark prediction. Alternatively, both networks 84, 86 are trained end-to-end or during a same training and/or the landmark output of the network 84 is used in training the GAN 86. Each GAN 40, 42 may be trained with a separate discriminator or one discriminator is used for the combination of generators (i.e., combination of GANs).

Any batch size may be used in training. In one embodiment, the batch size is 32 examples. In another embodiment, the batch size is 1 example. Smaller batch size may lead to higher loss and mean square error.

In one embodiment, the marker prediction network (i.e., network 84) takes the surface image as well as the predicted X-ray image as input and predicts the locations for all the markers. The network 84 is a U-Net like architecture trained to regress from a 3-channel input image (2 surface data channels, 1 X-ray image channel) to a 17-channel heatmap image by minimizing L2-loss or other loss. The landmark image is a heatmap corresponding to 17 anatomically meaningful landmarks, such as lung top, liver top, kidney center, etc.). The heatmap is a spatial distribution of likelihood of any given pixel or voxel being the landmark. For the heatmaps, each output channel compares with the given ground truth that includes a Gaussian mask (kernel radius=5, σ=1) centered at the given target location. Other radii and standard deviations may be used. Other images or spatial distributions than a heatmap may be used, such as providing binary labels for each landmark.

For an initial use, the topogram is not available for input to the landmark network 84. A default topogram for the application (e.g., upper torso imaging), noise, or other input may be used. In another approach, a GAN 82 is trained to output a topogram from the surface data. This GAN 82 provides the initial topogram as input to the landmark network 84. Where iterations are used, later topograms input to the landmark network 84 are from the topogram GAN 86. Alternatively, default, noise or other landmark image is input to the topogram GAN 86 as an initial step, where the topogram GAN 86 then outputs to the landmark network 84. Thus, the landmark network 84 receives the topogram from either the initialization GAN 82, the topogram GAN 86, or another source.

The proposed conditional image generation network of the GAN 86 is derived from a conditional GAN architecture. In one embodiment, a Wassertein GAN architecture conditioned on the skin surface is used. The generator with the U-Net architecture takes the surface image and marker heatmaps as input and outputs the synthetic X-ray image as the topogram. To stabilize the training, a Wasserstein loss with gradient penalty is used. Other losses with or without a gradient penalty may be used. The critic or discriminator takes the surface image and corresponding X-ray image as input. Alternatively, the critic or discriminator receives the surface images, marker maps (parameter space) and X-ray image as input to implicitly force a strong correlation between them.

Each of the networks 82, 84, 86 receive surface data as an input. In alternative embodiments, one or more of networks 82, 84, 86 do not use surface data as the input, such as the network 84 or the GAN 86. Additional, different, or fewer networks may be used, such as not including the initialization GAN 82. One or more of the network 82, 84, 86 may be a different image-to-image network.

With the stacked pipeline in FIG. 8, one or more of the landmarks may be moved by the user or by image processing. User input of a landmark or processor input is received. As a result, the landmark image for that channel is altered. Upon input to the topogram GAN 86, the topogram GAN 86 outputs a topogram based on the altered landmark image. To update the topogram, the other landmarks may move in a constrained fashion. For example, the lung bottom cannot be below the kidneys since that's physically not a possible setup. By reusing the predicted topogram from the GAN 86 in the stacked pipeline, the networks 84 and 86 ensure that the landmarks and topogram are consistent. If a landmark is updated, the rest of the landmarks are appropriately updated (if needed) by cycling the resulting topogram through the landmark network 84 and again predicting a topogram by the topogram GAN 86 based on the output landmark images. The topogram ensures physical correctness.

The stacked pipeline of FIG. 8 provides an image (e.g., topogram) parametrized by a set of spatially distributed markers. One or more of the markers may be manipulated in size and/or location while still providing realistic topograms. The manipulation of an image via markers (spatial parameters) uses learning a bijection mapping. The Marker Prediction network (MPN) (i.e., network 84) is trained to predict the parameters from the image contents, and the Conditional Image Generation network (CIGN) (i.e., GAN 86) is trained to predict the image contents given the parametrization. After initial predictions, the networks 84, 86 are iteratively applied (i.e., current output used as input in repeating cycles) until convergence. While parametrized images may be generated from noise, conditional image generation as naturally applied to the task of generating the X-ray images from 3D body surface data is used.

The stacked pipeline of FIG. 8 is trained sequentially, simultaneously, and/or end-to-end. Other training approaches may be used. In one embodiment, the landmark and topogram networks 84, 86 are separately pre-trained using the available ground truth data. The network 84, 86 are subsequently refined end-to-end to minimize the combined loss, defined as, $L=L_{MPN}+L_{CIGN}$ where, $L_{MPN}$ is the mean squared error (MSE) between the predicted and the ground truth heat maps for the markers and $L_{CIGN}$ is the MSE between the predicted and ground truth X-ray image.

For pre-training the landmark network 84 (i.e., Marker Prediction Network), the Adam or other optimizer minimizes the MSE loss. The initial learning rate is $10^{-3}$. During pre-training, the ground truth X-ray images with body surface images (i.e., surface data) are used as inputs. During the convergent training process, the input is replaced by the predicted X-ray image. This initially worsens the performance on the marker prediction network, but the network quickly recovers after a few epochs of convergent training.

For pre-training the topogram GAN 86 (i.e., Conditional Image Generation Network), surface images and ground truth landmark maps are input, using the Adam or other optimizer with an initial learning rate of $10^{-3}$. After pre-training, the RMSProp or other optimizer with a low learning rate of $10^{-5}$ is used. The gradient penalty variant of Wasserstein GAN (WGAN) may outperform the original WGAN with weight clipping. The architecture of the critic is similar to the encoder section of the generator network. In the case of WGAN, using a more complex critic may help training converge more quickly. During the convergent training, the network is iteratively updated using the predicted landmarks as input.

For the convergent training via iterative feedback, both networks are iteratively applied in succession until both reach the steady state during the test phase. This implicitly requires the networks to have a high likelihood of convergence during the training stage. A stable solution sits where both the markers and synthetic image are in complete agreement with each other, suggesting a bijection. One network is frozen while updating the weights of the other network using its own loss as well as the loss backpropagated from the other network. Thus, not only the networks get feedback from the ground truth, the networks also get feedback on how they helped each other (e.g., good markers give good X-ray image, and vice versa). The losses optimized by conditional image generation (CIGN) and marker prediction network (MPN) at each iteration are given by: $L_{CIGN}=L_{adv}(I_{gt}, I^i_{syn})+L_2(MPN(I^i syn, S), M_{gt})$ and $L_{MPN}=L_2(M^i, M_{gt})+L_1(I_{gt}, CIGN(M^i, S))$ where, CIGN(.) and MPN(.) are deep networks depicted in functional form, $I_{gt}$ and $M_{gt}$ are ground truth image and markers heat maps respectively, and $I^i_{syn}$ and $M^i$ are predicted images and markers heat maps at iteration i. The iterative approach to train the networks to facilitate convergence is through learning to cooperate instead of competing. Similar to GAN training, there is a possibility that the training may become unstable and diverge. The losses are weighted with a scale to avoid divergence. While the number of epochs required to reach convergence depends on how tightly the output of the two networks correlate, 50 epochs may be sufficient. Other numbers of epochs may be used. No significant (e.g., threshold amount) change in X-ray or in landmarks positions suggests or indicates convergence. Algorithm 1 below details one example pseudo-code for convergent training.

---
Algorithm 1 Convergent training
---

Require: : $\alpha$, the learning rate. $T_s$, the model generating X-ray from surface. $w_m$, initial MPN weights. $w_t$, initial CIGN weights. $\lambda_1$ and $\lambda_2$ loss scaling factors.
1: while $w_m$ and $w_t$ have not converged do
2:     Sample x a batch from the input data.
3:     Get $\hat{m}$, $\hat{t}$ ground truth landmarks and X-ray
4:     $t_1 \leftarrow T_s(x)$
5:     $x' \leftarrow \text{concat}(x, t_1)$
6:     $m_1 \leftarrow \text{MPN}(x')$
7:     $e_M \leftarrow \mathcal{L}_{MPN}(m_1, \hat{m})$
8:     $x' \leftarrow \text{concat}(x, m_1)$
9:     $t_2 \leftarrow \text{CIGN}(x')$
10:    $e_T \leftarrow \mathcal{L}_{CIGN}(t_2, \hat{t})$
11:    $g_{w_m} \leftarrow \nabla_{w_m} [e_M + \lambda_1 \cdot e_T]$
12:    $w_m \leftarrow w_m + \alpha \cdot \text{RMSProp}(w_m, g_{w_m})$
13:    $x' \leftarrow \text{concat}(x, m_2)$
14:    $m_2 \leftarrow \text{MPN}(x')$
15:    $e_M \leftarrow \mathcal{L}_{CIGN}(m_2, \hat{m})$
16:    $g_{w_t} \leftarrow \nabla_{w_t} [e_T + \lambda_2 \cdot e_M]$
17:    $w_t \leftarrow w_t + \alpha \cdot \text{RMSProp}(w_t, g_{w_t})$ To validate the convergent training, a random data sample is selected from the testing set, and the marker displacement across iterations is monitored. Without the convergent training, the markers may change across iterations.

The stacked networks of FIG. 8 are evaluated. 2045 full body CT images are collected from patients. The entire dataset is randomly split into a testing set of 195 images, a validation set of 108 images, and a training set with the rest. The 3D body surface meshes are obtained from the CT scans using thresholding and morphological image operations. The X-ray images are generated by orthographically projecting the CT images. All the data are normalized to a single scale using the neck and pubic symphysis body markers since these may be easily approximated from the body surface data. Using the PyTorch environment, the U-Net like networks are composed of four levels of convolution blocks, each consisting 3 repetitions of convolution, batch normalization, and ReLU. Each network has 27 convolutional layers with 32 filters in each layer.

Although the purpose of the convergent training is to ensure a tight correlation between X-ray and markers, the error statistics are computed with respect to the ground truth marker annotations provided by medical experts for landmark estimation. The convergent training helps improve the accuracy of the marker prediction network, though the improvement is not quantitatively significant (e.g., the mean Euclidean distance drops from 2.50 cm to 2.44 cm). The accuracy improves for some of the particularly difficult to predict markers, such as the tip of the sternum, since the convergent training facilitates more stable prediction. For example, in the case of the tip of the sternum, the error drops from 2.46 cm to 2.00 cm.

For the synthetic x-ray prediction, the pix2pix approach is used as a baseline for conditional image regression. L1-loss is used for training the generators. Using a receptive field of 34×34 achieves the lowest validation error. The batch size is gradually reduced from 32 to 1, enabling faster training in the beginning although with blurred results. As the training continues and the batch size is reduced to 1, more details are recovered. Using L1 error and the Multi-Scale Structural Similarity index (MS-SSIM) averaged over the entire testing set, WGAN with gradient prediction has a higher MSSSIM and lower L1 error than UNet, Pix2Pix, WGAN, and Conv-WGAN-GP. The convergent training may retain a high perceived image quality, while ensuring that the markers are strongly correlated with the X-ray image.

Figure 9:
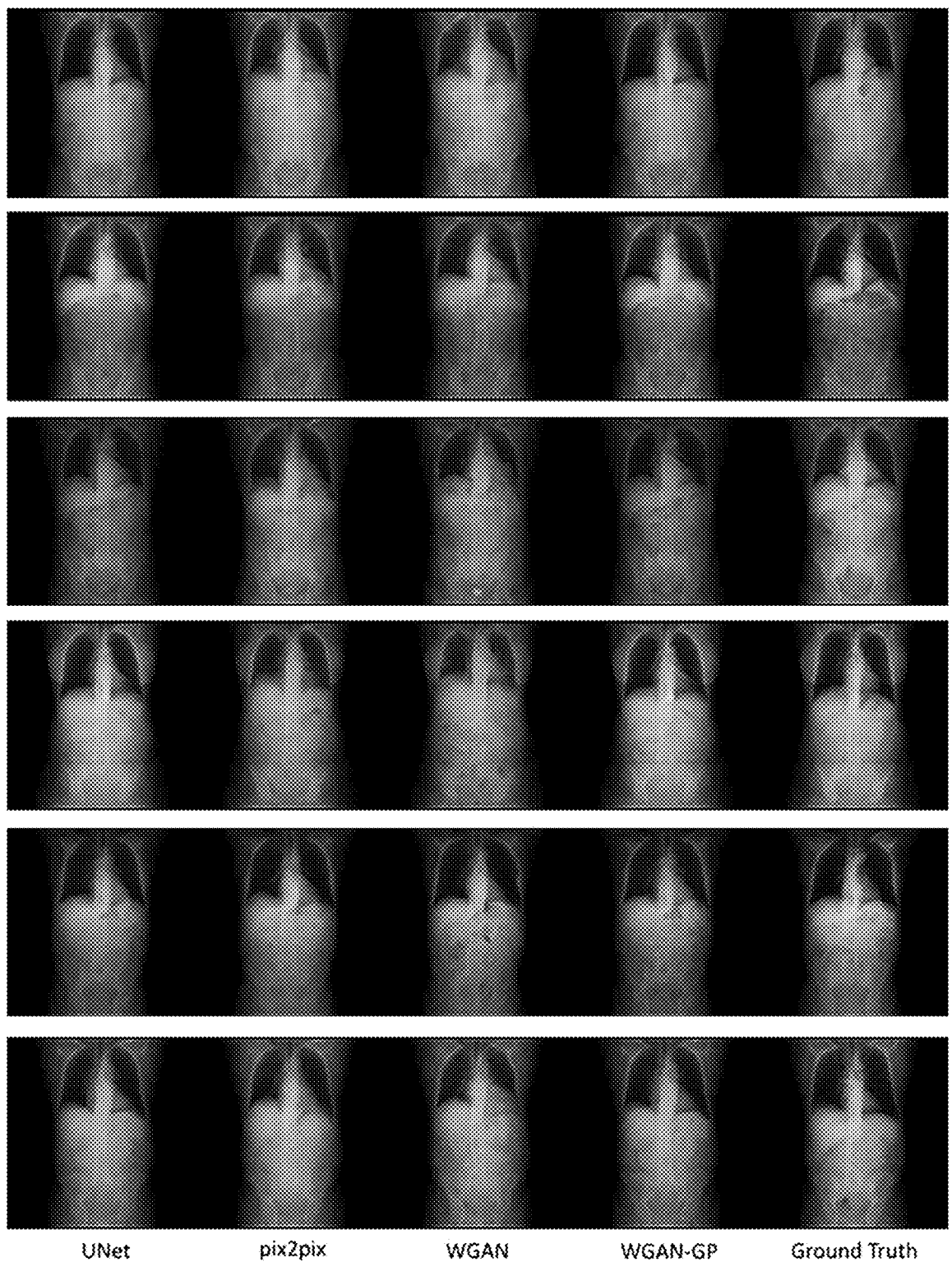
FIG. 9 shows example topograms predicted with various machine-learned networks.

FIG. 9 shows predicted X-ray images for six different patients and corresponding surface images. Compared to the ground truth, synthetic X-ray images have high accuracy in certain regions such as upper thorax and less accuracy in other regions such as lower abdomen where the variance is known to be significantly higher. The images generated using the WGAN-GP are sharper around organ contours and spine and pelvic bone structures are much clearer.

Referring again to FIG. 1, a display device displays the topogram in act 14. Where several iterations of the topogram are generated, the topogram after a given number of iterations and/or convergence is displayed. Other predicted topograms may be displayed.

The display is a visual output. The image processor generates an image. A topogram image is generated and displayed on the display. The image may be output to a display, into a patient medical record, and/or to a report.

The image is generated from the scalar values or intensities of the topogram. The scalar values are mapped to display values, such as RGB values. A grayscale or color image of the topogram is generated. In other embodiments, the topogram is predicted as display values. Since the topogram is a projection, the image is a 2D image. The image of the topogram shows the patient shape as well as positions of one or more organs. One or more landmarks may be highlighted, such as using graphics (e.g., boxes, dots, lines, or another marker).

The topogram may be used for diagnosis or other purpose by the user. For example, the topogram is used to position a patient, such as moving the patient along a longitudinal axis so that a given landmark or organ is centered with respect to the medical scanner.

In act 16, the image processor configures the medical scanner based on the topogram. The medical scanner may configure itself. The landmarks may be used, or organ location is detected from the topogram. Alternatively, the user configures the medical scanner based on the topogram by entry with one or more controls.

The prediction of certain internal anatomical structures may assist in planning a medical scan. The topogram may be used to plan for scanning by any modality, such as CT, MR, fluoroscopy or ultrasound. For CT scanning, the topogram may used to determine the scan range to obtain topogram or full CT scan, depending upon which organ needs to be scanned and how accurately the nearby structures may be predicted. The location of internal anatomical structures reflected in the topogram may assist is coil placement for MR scanning. For ultrasound scanning, the topogram may assist in the probe guidance by providing approximate position of the various organs. For fluoroscopy using dyna-CT scans, the topogram may be useful for positioning the patient and/or the scanner.

As radiation exposure is considered harmful, X-ray images are often acquired with a limited field of view, only covering a certain body region (e.g., thorax or abdomen). Using parametric images, the X-ray image of the entire body may be reconstructed or predicted such that the predicted topogram is consistent with the partial yet real image. The reconstructed X-ray image may be used for acquisition planning in subsequent or future medical scans. Using the reconstructed X-ray, the scan region may be specified more precisely, thus potentially reducing the radiation exposure.

To reconstruct the complete X-ray, a parametrized X-ray image of the patient is generated from the surface data. The predicted X-ray may not always correspond to the true internal anatomy. Using the markers on the parametrized image, the markers may be adjusting until the synthetic X-ray matches the real one where they overlap. Once the markers are adjusted, the complete X-ray is generated together with all the markers.

The predicted topogram may be used for anatomical anomaly detection. The predicted topogram generates a representation of healthy anatomy learned from healthy patients. A real or actual X-ray image of the patient may be compared with the predicted topogram. By quantifying the difference between the real X-ray image and the predicted one, any anatomical anomalies may be detected. For example, a missing lung or an added implant are highlighted by subtraction. While the anatomical anomaly is easier to identify, the proposed approach with higher resolution imaging may be used to suggest candidates for lung nodules or other pathological conditions.

Due to privacy and health safety issues, medical imaging data is difficult to obtain, which creates a significant barrier for data driven analytics such as deep learning. The topogram prediction may be employed to generate realistic training data. The ability to spatially reposition the landmarks and generate a corresponding topogram is used to create a varied sampling for training. Parametrized X-ray images offer an approach to generate medical image training data. The spatial parametrization offers controlled perturbations such as generating data variations with lungs of certain sizes. For tasks such as marker detection, since the image manifold is smooth, it's possible to generate training data (for augmentation) together with annotations, by annotating the marker in one image and tracking it in the image domain as it is perturbed along the image manifold.

In one example of generating training data, the left lung bottom landmark is manually annotated in 50 synthetic X-ray images to be used for training data. For evaluation, 50 ground truth X-ray images are manually annotated. To generate the augmented training dataset, 100 random perturbations are generated from the annotated parametrized images by allowing the marker to move within a certain range. Since the image manifold is smooth, as the position of the marker changes in the perturbed image, the annotation propagates using coefficient normed template matching. A Fully Convolutional Network is trained to regress the marker location, depicted as a Gaussian mask, from the X-ray image. The Adam optimizer with an initial learning rate of $10^{-3}$ is used. To measure the usefulness of data generated using parametrized images, a baseline training dataset is created by augmenting the 50 training images using 100 random translations. After only 5 epochs, the model trained with the parametrized training data had a 0.99 cm mean error on the testing set, compared to 8.75 cm for the baseline. After 25 epochs, the baseline has a mean error of 1.20 cm, while the network trained on data with parametrized perturbations has a much lower 0.68 cm error.

In act 18, the configured medical scanner scans the patient. The patient is imaged. The imaging is performed based on the configuration of the medical scanner. The scan range, focus, field of view, and/or other imaging parameters are based on the topogram, so the scanning is based on the topogram. The resulting image from the scanning more likely shows the region of interest. Ionizing radiation from the scanning may be limited based on the configuration using the topogram.

Figure 10:
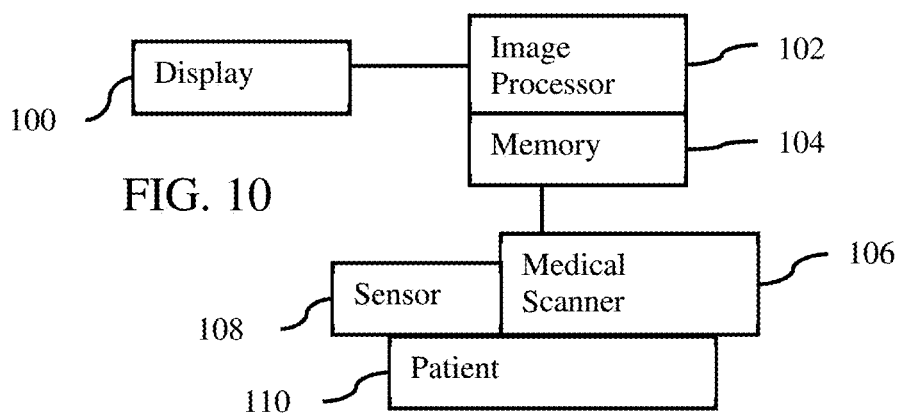
FIG. 10 is a block diagram of one embodiment of a system for topogram prediction.

FIG. 10 shows a medical imaging system for topogram prediction. The medical imaging system includes the display 100, memory 104, and image processor 102. The display 100, image processor 102, and memory 104 may be part of the medical scanner 106, a computer, server, workstation, or other system for image processing medical images from a scan of a patient. A workstation or computer without the medical scanner 106 may be used as the medical imaging system. The medical imaging system also includes the sensor 108 for sensing an outer surface of a patient.

Additional, different, or fewer components may be provided. For example, a computer network is included for remote topogram image generation of locally captured surface data or for local topogram image generation from remotely captured surface data. The network is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks).

The sensor 108 is a depth sensor. LIDAR, 2.5D, RGBD, stereoscopic optical sensor, or other depth sensor may be used. One sensor 108 is shown, but multiple sensors may be used. A light projector may be provided. The sensor 108 may include a separate processor for depth measurements from images, or the image processor 102 determines the depth measurements from images captured by the sensor 108.

The sensor 108 is directed to the patient 110. The sensor 108 may be part of or connected to the medical scanner 106 or is separate from the medical scanner 106.

The sensor 108 is configured to measure depths to a patient. The depths are distances from the sensor 108 or other location to the patient at various locations on the patient. Any sample pattern over the patient may be used. The sensor 108 outputs depth measurements and/or a surface image. The image processor 102 or another processor may fit a model to the sensor output to provide surface data. Alternatively, the sensor 108 outputs the surface data as the measurements.

The image processor 102 is a control processor, general processor, digital signal processor, three-dimensional data processor, graphics processing unit, application specific integrated circuit, field programmable gate array, digital circuit, analog circuit, combinations thereof, or other now known or later developed device for processing medical image data. The image processor 102 is a single device, a plurality of devices, or a network. For more than one device, parallel or sequential division of processing may be used. Different devices making up the image processor 102 may perform different functions, such as applying different GANs or applying the GANs and configuring the medical scanner 106. In one embodiment, the image processor 102 is a control processor or other processor of a medical diagnostic imaging system, such as the medical scanner 106. The image processor 102 operates pursuant to stored instructions, hardware, and/or firmware to perform various acts described herein.

The image processor 102 is configured to train a machine learning architecture. Based on a user provided or other source of the network architecture and training data, the image processor 102 learns features for encoders, decoders, discriminators, or other network parts to train the network. The result of the training is a machine-learned network or networks for topogram prediction with or without landmark parameterization.

Alternatively or additionally, the image processor 102 is configured to apply one or more machine-learned networks. For example, a GAN is applied to surface data from the sensor. The machine-learned generative network is applied to surface information. Based on the previous training, the network generates a topogram in response to application of the surface data (e.g., depth information from measured depths). One network may output a landmark probability map (e.g., heatmap), and another network may output the topogram based on input of the landmark probability map. Both networks may receive depth information for the outside of the patient as inputs. As another example, the image processor 102 is configured to generate the topogram using a WGAN having been trained using a gradient penalty.

The image processor 102 is configured to generate an image. The topogram output from the GAN may be an image. Alternatively, the scalar values forming the topogram are mapped to display values. Annotations or graphics, such as for the landmarks, may be added to the image.

The display 100 is a CRT, LCD, projector, plasma, printer, tablet, smart phone or other now known or later developed display device for displaying the output, such as a topogram. The display 100 displays a medical image topogram generated from the depth information.

The sensor measurements, fit shape model, surface data, network definition, features, machine-learned network, landmark images, output topogram, and/or other information are stored in a non-transitory computer readable memory, such as the memory 104. The memory 104 is an external storage device, RAM, ROM, database, and/or a local memory (e.g., solid state drive or hard drive). The same or different non-transitory computer readable media may be used for the instructions and other data. The memory 104 may be implemented using a database management system (DBMS) and residing on a memory, such as a hard disk, RAM, or removable media. Alternatively, the memory 104 is internal to the processor 102 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 104). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical scanner 106 is a medical diagnostic imaging system configured to scan a volume of a patient and generate anatomical information from the scan. The medical scanner 106 is a CT, MR, PET, SPECT, X-ray, or ultrasound scanner.

The medical scanner 106 is configured to generate anatomical information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on a topogram generated from the surface data rather than scanning by the medical scanner 106, one or more settings of the medical scanner 106 are set. The patient 110 is imaged by the medical scanner 106 using the settings. In alternative embodiments, scan data from the medical scanner 106 is used to determine the surface data, such as by fitting a statistical shape model that includes a skin mesh to the scan data.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for obtaining a predicted synthetic topogram from surface data in a medical imaging system, the method comprising:
   capturing, with a sensor, the surface data, wherein the surface data represents an outer surface of a patient;
   generating, by an image processor, the predicted synthetic topogram by a machine-learned generative adversarial network in response to input of the surface data captured by the sensor to the machine-learned generative adversarial network, wherein the predicted synthetic topogram includes an internal organ of the patient, and wherein the predicted synthetic topogram represents a two-dimensional projection of the internal organ of the patient; and
   displaying, by a display device, the predicted synthetic topogram.

2. The method of claim 1 wherein capturing comprises capturing with the sensor being a depth sensor.

3. The method of claim 1 wherein capturing comprises capturing with the sensor being a camera where the surface data based on optical measurements.

4. The method of claim 1 wherein generating further comprises fitting a statistical shape model to the output of the sensor for the outer surface, the surface data comprising (a) depths from the fit statistical shape model and (b) a projection of the outer surface or a thickness.

5. The method of claim 1 wherein generating comprises generating with the machine-learned generative adversarial network comprising a fully convolutional network with an encoder and a decoder.

6. The method of claim 5 wherein the encoder and the decoder comprise a U-Net with skip connections between the encoder and the decoder.

7. The method of claim 1 wherein generating comprises generating with the machine-learned generative adversarial network being a stacked U-Net.

8. The method of claim 1 wherein generating comprises generating with the machine-learned generative adversarial network having been trained with an L1 loss.

9. The method of claim 1 wherein generating comprises generating with the machine-learned generative adversarial network including a first generator for generating a first X-ray image from the surface data, a second generator for generating a landmark image from the first X-ray image or a second X-ray image and the surface data, and a third generator for generating the second X-ray image from the surface data and the landmark image, the second X-ray image comprising the predicted synthetic topogram.

10. The method of claim 9 wherein generating comprises iteratively using the second and third generators.

11. The method of claim 9 further comprising:
receiving user input of a landmark location of a first landmark;
wherein generating comprises generating the predicted synthetic topogram with the first landmark constrained to the landmark location.

12. The method of claim 1 wherein generating comprises generating with the generative adversarial network having been trained with a gradient penalty.

13. The method of claim 1 further comprising:
configuring a medical scanner based on the predicted synthetic topogram; and
imaging, by the medical scanner, the patient as configured based on the predicted synthetic topogram.

14. A method for estimated synthetic topogram prediction from surface data in a medical imaging system, the method comprising:
capturing, with a sensor, an outer surface of a patient;
generating, by an image processor, the estimated synthetic topogram by first and second machine-learned networks in response to input of the surface data captured by the sensor to the first and second machine-learned networks, the surface data being from an output of the sensor for the outer surface, the estimated synthetic topogram representing an internal organ of the patient as a projection through the patient, the first machine-learned network outputting a spatial marker map, and the second machine-learned network outputting the estimated synthetic topogram based on the surface data and the spatial marker map, wherein the estimated synthetic topogram includes an internal organ of the patient, and wherein the estimated synthetic topogram represents a two-dimensional projection of the internal organ of the patient; and
displaying, by a display device, the estimated synthetic topogram.

15. The method of claim 14 wherein generating further comprises iteratively using the first and second machine-learned networks, the first machine-learned network outputting the spatial marker map in response to input of the estimated synthetic topogram and the surface data, and wherein displaying comprises displaying a final one of the estimated synthetic topograms from the iterations.

16. The method of claim 15 wherein generating comprises generating with a third machine-learned network, the third machine-learned network outputting an initial estimated synthetic topogram for the iterating to the first machine-learned for an initial iteration.

17. The method of claim 14 wherein generating comprises generating with the first and second machine-learned networks comprising Wasserstein generative adversarial networks having been trained with gradient penalties.

18. A medical imaging system for estimated synthetic topogram prediction, the medical imaging system comprising:
a depth sensor configured to measure depths from the sensor to a patient;
an image processor configured to apply a machine-learned generator of a trained generative adversarial network to depth information from the depths, the machine-learned generator having been trained to generate the estimated synthetic topogram from the depth information, wherein the estimated synthetic topogram includes an internal organ of the patient, and wherein the estimated synthetic topogram represents a two-dimensional projection of the internal organ of the patient; and
a display configured to display the estimated synthetic topogram.

19. The medical imaging system of claim 18 wherein the generative adversarial network comprises a Wasserstein generative adversarial network having been trained using a gradient penalty.

20. The medical imaging system of claim 18 wherein the machine-learned generator comprises first and second generators, the first generator configured to output a landmark probability map and the second generator configured to output the estimated synthetic topogram based on input of the depth information and the landmark probability map.

* * * * *